(12) United States Patent
Marshall

(10) Patent No.: US 7,004,930 B2
(45) Date of Patent: Feb. 28, 2006

(54) NEEDLE PROTECTION DEVICES WITH MUTUALLY FACING ABUTMENTS

(75) Inventor: Jeremy Marshall, Oxford (GB)

(73) Assignee: Owen Mumford Limited, Oxford (GB)

( * ) Notice: Subject to any disclaimer, the term of this patent is extended or adjusted under 35 U.S.C. 154(b) by 0 days.

(21) Appl. No.: 10/332,138

(22) PCT Filed: Jul. 5, 2001

(86) PCT No.: PCT/GB01/03001

§ 371 (c)(1),
(2), (4) Date: Sep. 29, 2003

(87) PCT Pub. No.: WO02/04053

PCT Pub. Date: Jan. 17, 2002

(65) Prior Publication Data

US 2004/0064103 A1    Apr. 1, 2004

(30) Foreign Application Priority Data

Jul. 6, 2000    (GB) .................................... 0016516

(51) Int. Cl.
    *A61M 5/32*    (2006.01)
(52) U.S. Cl. .................................... 604/198
(58) Field of Classification Search ................ 604/181, 604/187, 192, 197, 198, 263; 128/919
    See application file for complete search history.

(56) References Cited

U.S. PATENT DOCUMENTS

| | | |
|---|---|---|
| 4,911,693 A | 3/1990 | Paris |
| 5,242,401 A | 9/1993 | Colsky |
| 5,389,085 A | 2/1995 | Alession et al. |
| 5,609,577 A | 3/1997 | Smedley et al. |
| 5,688,241 A | 11/1997 | Asbaghi |

FOREIGN PATENT DOCUMENTS

| | | |
|---|---|---|
| EP | 0 749 758 A | 12/1996 |
| GB | 1 133 555 | 11/1997 |
| WO | WO 99 25402 | 5/1999 |
| WO | WO 00 25845 | 5/2000 |

*Primary Examiner*—LoAn H. Thanh
(74) *Attorney, Agent, or Firm*—Young & Thompson

(57) ABSTRACT

A syringe holder has a barrel (1) with a needle shroud (4) telescopic into its leading end and urged forwardly by a spring (5). The shroud is rotatable into several set positions, being located by snap action of a nib (18) into longitudinal grooves within a forward extension (3) of the barrel (1). An abutment (21,20) on the shroud is thereby aligned with a selected one of several abutments (12,9,14) within the barrel, these all being at different axial positions. One setting prevents needle exposure; the others permit different amounts of needle exposure as the barrel (1) is urged forwardly during an injection.

12 Claims, 1 Drawing Sheet

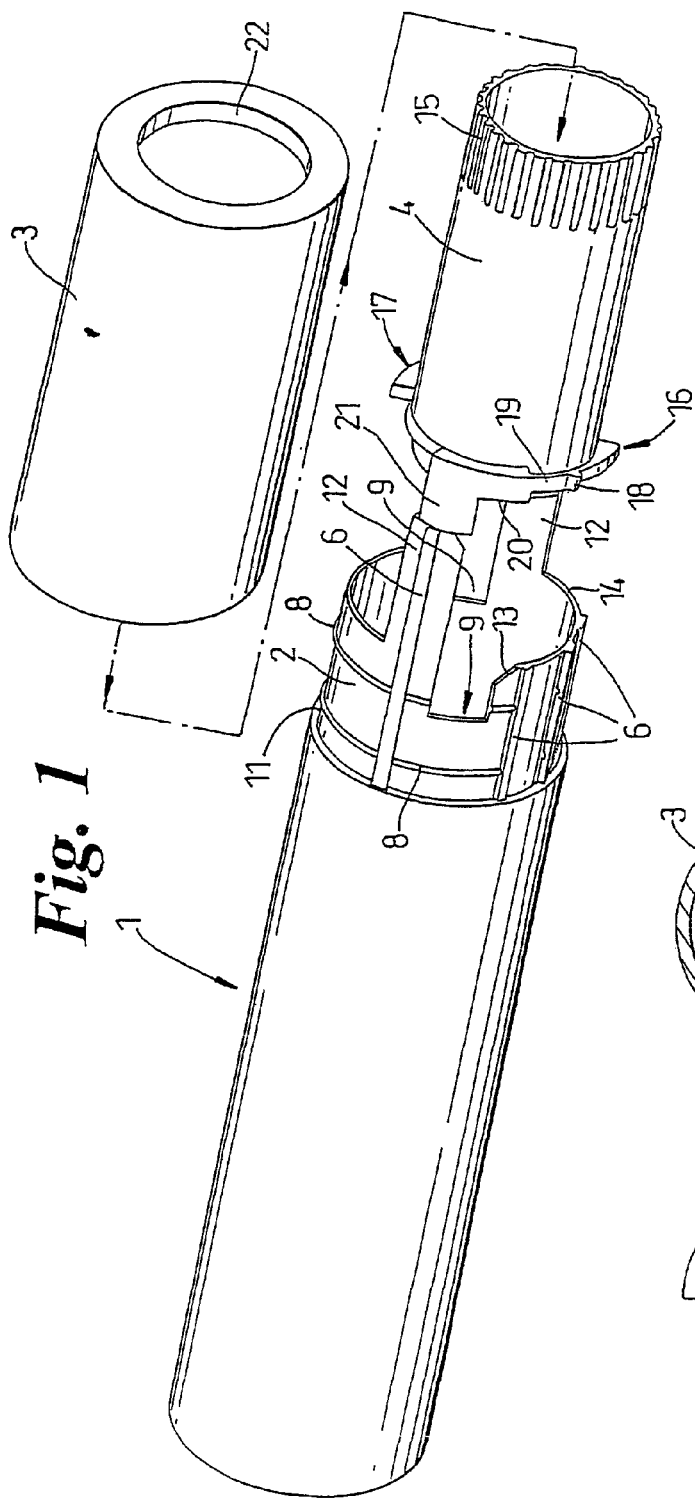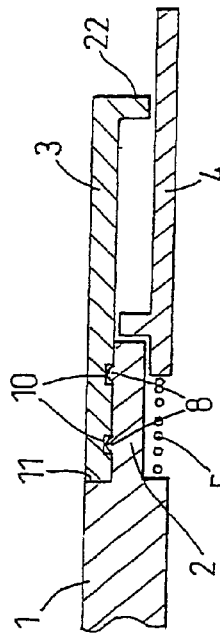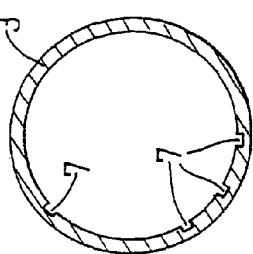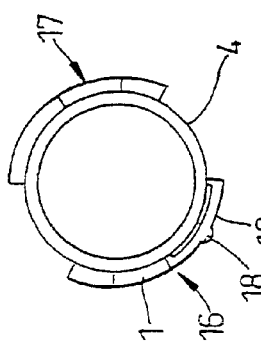

NEEDLE PROTECTION DEVICES WITH MUTUALLY FACING ABUTMENTS

BACKGROUND OF THE INVENTION

This invention relates to needle protection devices.

A medical syringe is often placed in a pen-like firing device or a holder of barrel form. The more sophisticated devices have a trigger which, when actuated, causes the dose to be administered automatically. The barrel-like holders make handling the syringe easier.

But whatever the syringe may be mounted in, its needle has to project from the forward end, at least at the time of administering the dose. At other times, it is advisable for the syringe either to be retracted within its holder or for a shroud to be placed over the needle.

It is not always desirable to have the needle project to the same extent each time an injection is made. Sometimes, the injection should be deep into the flesh, and at other times it should be shallow.

It is the aim of this invention to provide a needle shroud arrangement which will protect the needle before and after use, but which can be adjusted to set the required depth of penetration.

SUMMARY OF THE INVENTION

According to the present invention there is provided a needle shroud assembly for a syringe holder, the assembly comprising a barrel and a tubular needle shroud captively telescoped into the forward end of the barrel, there being mutually facing abutments on the barrel and the shroud to limit the rearward telescopic movement of the shroud by different amounts according to its rotational position in relation to the barrel.

Preferably, the barrel and shroud have mutually interengageable detents to register the shroud in particular rotational positions, each interengagement allowing relative axial movement of the barrel and shroud so that abutments associated with the rotational position selected can engage. Conveniently, the detents are axially parallel grooves in either the barrel or shroud and a projection on the shroud or barrel that can snap into and out of the grooves. Advantageously the projection is on a thin element integrally moulded with the shroud, the grooves being in the barrel.

Preferably, the barrel has a set of forward facing internal abutments at different circumferential and axial positions, the shroud having a rearward facing abutment.

The barrel may have a main body with a reduced leading end and an extension that retentively telescopes over this leading end and which is adapted to keep the shroud captive. The set of forward facing abutments can then be provided by the reduced leading end.

The extension can be circumferentially located by longitudinal ribs on the reduced leading end engaging complementary grooves in the extension, and these may extend beyond the main body of the barrel to provide the detents for the projection on the shroud. The shroud will generally have a forward spring bias to a limiting position where the needle of a syringe within the barrel is concealed within the shroud. There will then be automatic protection of the needle before and after injection, and the shroud will retract by the amount allowed as the syringe is applied.

BRIEF DESCRIPTION OF THE DRAWINGS

For a better understanding of the invention, one embodiment will now be described, by way of example, with reference to the accompanying drawing, in which:

FIG. 1 is a perspective exploded view of a syringe holder with a needle shroud, FIG. 2 is an end view of the shroud, and FIG. 3 is a cross-section of an outer casing of the holder, and FIG. 4 is a detail, in longitudinal section, of the forward part of the holder.

DESCRIPTION OF THE PREFERRED EMBODIMENTS

The syringe holder has a barrel with a main body 1 having a reduced forward end portion 2 and, an extension 3 which fits over that portion 2. An adjustable tubular needle shroud 4 captive to the forward end of the barrel by the extension 3, and a spring 5 urges the shroud 4 forwards. The manner of location of the syringe within the barrel is not material to this invention; suffice it to say that it is housed co-axially with its needle projecting forwardly from the barrel.

The portion 2 has external longitudinal ribs 6 which engage in corresponding internal grooves 7 in the extension 3. Their numbers and circumferential spacing relate to the geometry of the stepped forward end of the portion 2 and the rear end configuration of the shroud 4 for reasons to be described below, and the grooves 7 are longer than their complementary ribs 6. The portion 2 also has annular ribs 8, less prominent than the ribs 6, around its forward end, the foremost one being interrupted by two diametrically opposed recesses 9 in the end of the portion 2. The extension 3 has complementary annular grooves 10 and the plastics material of which the main body 1,2 of the barrel and the extension 3 are made allows the latter to be snap fitted over the end portion 2 so that it abuts the shoulder 11 where the portion 2 begins, thus providing a smooth continuation of the barrel.

On one circumferential side of each recess 9 the portion 2 extends into a finger 12, bevelled at its tip, and along one of these fingers runs one of the ribs 6. On the other circumferential side of each recess 9 its mouth widens at a bevel 13 and then there is an arcuate, intermediate section 14 round to the opposite finger 12. The other ribs 6 terminate at points along one of these sections.

The shroud 4 projects from the extension 3 and is axially grooved at 15 at its forward end to afford a good grip. Its rear end has a complex flange in two arcuate sections 16 and 17 to co-operate with the forward end portion 2 of the body 1. The section 16 steps out from the shroud 4 to an extent such that its outer cylindrical envelope corresponds generally to the interior surface or the extension 3 and the exterior surface of the portion 2.

But it has an outwardly projecting nib 18 at the centre of a thin bridge 19 standing away from the main body of the shroud over about half the arcuate length of the section 16. This bridge 19 is reduced enough to form a spring (the shroud being an integral moulding of plastics material) and the nib 18 can thereby have snap action in and out of the grooves 7 in the extension 3. The remaining portion of the section 16, from one end of the bridge 19, first doubles in thickness, in the rearward axial direction, to provide a step 20 and then extends further rearwardly in a projection 21.

The other similar section 17 lacks the bridge 19 and nib 18, that portion being solid, but it could exactly duplicate the section 16.

The shroud 4 is normally urged forwards by the spring 5 so that the flange sections 16, 17 abut an inturned flange 22 at the mouth of the extension 3. The shroud 4 is circumferentially located by the nib 18 engaging in one of the grooves 7 whose forward ends are exposed beyond the portion 2. The grooves 7 and nib 18 are denoted herein as mutually interchangeable detents.

If it is the groove 7 engaged by the rib 6 nearest the bevel 13, then the projections 21 align with the ends of the fingers 12. This prevents or severely limits the rearward movement of the shroud, which then gives full protection to the needle of a syringe housed in the barrel.

By turning the shroud 4 left handed (as seen in FIG. 1) the nib 18 snaps out of one groove 7 into the next, which aligns the projections 21 with the recesses 9. The shroud can then be pushed rearwardly against the spring 5 until the projections 21 seat in those recesses, while the fingers 12 pass through the gaps between flange sections 16 and 17 to lie between the shroud 4 and the extension 3. This is the maximum retracted position of the shroud and gives the greatest needle exposure.

For less needle exposure, the shroud is released and turned, again left handed, until the nib 18 engages in the third groove 7. The projections 21 are then opposite the ends of the intermediate sections 14 adjacent the bevels 13. This further rotation is not impeded by the fingers 12: the gaps between the ends of the flange sections 16 and 17 are sufficiently large.

For even less needle exposure, the shroud 4 is released and rotated until the nib 18 engages the groove 7 with which the ribbed finger 12 co-operates. Then the ends of the fingers 12 will be opposite the bridge 19 and the corresponding portion of the section 17, whether that be solid or another bridge.

The recesses 9, fingers 12, intermediate sections 14, and projections 21 are denoted herein as mutually facing abutments. Prior to use, the shroud 4 is turned to align the abutments which will meet to give the desired needle exposure, and as the syringe is offered up the forward end of the shroud 4 meets the skin surrounding the intended puncture point. While the spring/barrel assembly is pushed forwards to make the needle penetrate, the shroud remains static and stops the barrel with the needle at the intended depth within the patients' flesh. On withdrawal, the spring 5 pushes the shroud 4 forwards relative to the barrel, and thereby keeps the needle protected.

There can be marks on the extension 3 and exposed part of the shroud 4 to help the user make the correct adjustment.

It may in some circumstances be preferred to have the spring bias in the opposite direction, urging the shroud rearwardly. It would then normally be set at the position shown in FIG. 1, where the needle would not be exposed, and before injection the user would rotate the shroud to the required setting and let it go. The spring (acting between the flange 22 and the composite flange 16, 17) would then push the shroud back so that the needle was exposed by the desired amount.

It would also be possible to reverse the abutment and rib and groove arrangements. The set of abutments could be at different axial positions on the shroud rather than on the barrel and the equivalent of the finger 12 would then be on the barrel. And there could be grooves instead of ribs 6 and ribs instead of grooves 7, with depressions in the shroud 4 into which those ribs could snap.

What is claimed is:

1. A needle shroud assembly for a syringe holder, comprising:
   a barrel and a tubular needle shroud captively telescoped into a forward end of the barrel, there being mutually facing abutments to limit rearward telescopic movement of the shroud by different amounts, first ones of said abutments being on the barrel and a second one of said abutments being on the shroud, said first abutments having differing relative longitudinal positions and differing rotational positions about the axis of the barrel to define the different amounts,
   the shroud being rotatable about said axis to bring said second abutment into direct alignment with a selected one of said first abutments, whereby the shroud is movable longitudinally into direct contact with a said selected abutment by one of the different amounts.

2. The needle shroud assembly as claimed in claim 1, wherein the barrel and shroud have mutually interengageable detents to register the shroud in particular rotational positions, each interengagement allowing relative axial movement of the barrel and shroud so that ones of said first and second abutments associated with the rotational position selected can engage.

3. The needle shroud assembly as claimed in claim 2, wherein the detents are axially parallel grooves in either the barrel or shroud and a projection on the shroud or barrel that can snap into and out of the grooves.

4. The needle shroud assembly as claimed in claim 3, wherein the projection is on a thin element integrally moulded with the shroud, the grooves being in the barrel.

5. The needle shroud assembly as claimed in claim 1, wherein said first abutments comprise a set of forward facing internal abutments at different circumferential and axial positions, the shroud having a rearward facing said second abutment.

6. The needle shroud assembly as claimed in claim 1, wherein the barrel has a main body with a reduced leading end and an extension that retentively telescopes over this leading end and which is adapted to keep the shroud captive.

7. The needle shroud assembly as claimed in claim 5, wherein the set of forward facing abutment is provided by a reduced leading end of the main body part of the barrel.

8. The needle shroud assembly as claimed in claim 6, wherein the extension is circumferentially located by longitudinal ribs on the reduced leading end engaging complementary grooves in the extension.

9. The needle shroud assembly as claimed in claim 3, wherein said grooves extend beyond the main body of the barrel to provide detents for a projection on the shroud.

10. The needle shroud assembly as claimed in claim 1, wherein the shroud has a forward spring bias to a limiting position where the needle of a syringe within the barrel is concealed within the shroud.

11. A needle shroud assembly for a syringe holder, comprising:
   a barrel and a tubular needle shroud captively telescoped into a forward end of the barrel; and
   mutually facing abutments that limit rearward telescopic movement of the shroud by different amounts according to relative positions of said abutments about an axis of the barrel, first ones of said abutments being on the barrel and a second one of said abutments being on the shroud,
   wherein the shroud is rotatable about said axis to bring said second abutment into alignment with a selected one of said first abutments so that the shroud is movable into direct contact with said selected abutment, wherein the barrel has a main body with a reduced leading end and an extension that retentively telescopes over this leading end and which is adapted to keep the shroud captive, and wherein the extension is circumferentially located by longitudinal ribs on the reduced leading end engaging complementary grooves in the extension.

12. A needle shroud assembly for a syringe holder, comprising:

a barrel and a tubular needle shroud captively telescoped into a forward end of the barrel; and mutually facing abutments that limit rearward telescopic movement of the shroud by different amounts according to relative positions of said abutments about an axis of the barrel, first ones of said abutments being on the barrel and a second one of said abutments being on the shroud, wherein the shroud is rotatable about said axis to bring said second abutment into alignment with a selected one of said first abutments so that the shroud is movable into direct contact with said selected abutment, wherein said first abutments comprise a set of forward facing internal abutments at different circumferential and axial positions, the shroud having a rearward facing said second abutment, and wherein the set of forward facing abutments is provided at a reduced leading end of a main part of the barrel.

* * * * *